United States Patent [19]

Goring et al.

[11] 4,225,607

[45] Sep. 30, 1980

[54] PHARMACEUTICAL COMPOSITION CONTAINING A XANTHINE DERIVATIVE

[75] Inventors: Joachim E. Goring; Peter P. Ochlich, both of Gronau, Fed. Rep. of Germany

[73] Assignee: Johann A. Wulfing, Fed. Rep. of Germany

[21] Appl. No.: 38,564

[22] Filed: May 14, 1979

[51] Int. Cl.$^2$ .................................... A61K 31/52
[52] U.S. Cl. ............................................ 424/253
[58] Field of Search ................................. 424/253

[56] References Cited

PUBLICATIONS

Chem. Abst., vol. 86 (1977)–78680s.

*Primary Examiner*—Stanley J. Friedman
*Attorney, Agent, or Firm*—Jacobs & Jacobs

[57] ABSTRACT

It has been found that 1,3-di-n-butyl-7-(2-oxopropyl)xanthine is a particularly effective agent for increasing oxygen partial pressure and contractility in ischaemic and skeletal muscle. Pharmaceutical compositions containing 1 to 30 mg of this agent are described.

8 Claims, No Drawings

PHARMACEUTICAL COMPOSITION CONTAINING A XANTHINE DERIVATIVE

The present invention relates to pharmaceutical compositions containing 1,3-di-n-butyl-7-(2-oxopropyl)-xanthine.

British Patent Specification No. 1441562 referred to the compounds of the formula (I):

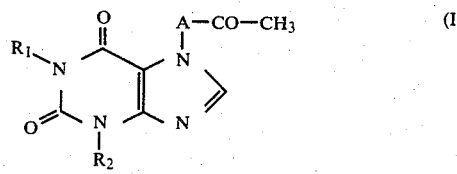

wherein $R_1$ and $R_2$ which may be the same or different, each represents a straight-chain or branched-chain alkyl radical of 2 to 6 carbon atoms, or a cyclohexyl, alkoxyalkyl or hydroxyalkyl radical, and A represents a hydrocarbon radical having up to 4 carbon atoms which may be substituted by a methyl group. The compounds of the formula (I) were described as effective in increasing the blood flow through skeletal muscles while at the same time showing low toxicity. The compound of the formula (I) said to be preferred was that wherein $R_1$ is an n-butyl group, $R_2$ is an n-butyl group and A is a $CH_2CH_2$ group. That compound was shown to be highly effective. German Patent application No. 2462367 indicates that the compounds of the formula (I) may in general be employed as unit doses of about 200–600 mgs so that they would be expected to be used at a similar dose to known agents such as pentoxyphylline. The published low oral toxicity of xanthines such as pentoxyphylline and the compound of the formula (I) where $R_1$ and $R_2$ are n-butyl groups and A is a $CH_2CH_2$ group means that such high doses are acceptable.

It has now been discovered that one compound within formula (I) is extremely potent in increasing oxygen tension and contractility is ischaemic and skeletal muscle. These properties reflect an improvement in the metabolic status of the tissue which in turn makes the compound of great potential use as an agent for the treatment of peripheral vascular disease such as intermittent claudication. This compound has a low acute toxicity so that the conventional high doses would have been expected to be used in the clinic. However the extremely high potency of this compound allows its use in surprisingly low dose.

Accordingly, the present invention provides a pharmaceutical composition which comprises 1 to 30 mg of 1,3-di-n-butyl-7-(2-oxopropyl)xanthine and a pharmaceutically acceptable carrier therefor.

More suitably the composition of this invention will contain from 2 to 25 mgs of 1,3-di-n-butyl-7-(2-oxopropyl)xanthine and preferably from 2.5 to 20 mgs of 1,3-di-n-butyl-7-(2-oxopropyl)xanthine, for example from 5 to 15 mgs.

Thus suitable compositions of this invention may contain about, for example, 2.5, 5, 7.5, 10, 12.5, 15, 17.5 or 20 mgs of 1,3-di-n-butyl-7-(2-oxopropyl)xanthine.

The compositions of this invention may be administered one or more times a day so that the daily dose is in the region of 2.5–90 mgs, and more usually 5–50 mgs, for example about 10–40 mgs. The composition is often administered twice or three times a day.

Generally the compositions of this invention will be adapted for administration by injection or for oral administration.

Although 1,3-di-n-butyl-7-(2-oxopropyl)xanthine is only sparingly soluble in aqueous media the enhanced potency of the compound renders it suitable for use in injectable solutions, for example in aqueous solution.

Thus one favoured aspect of this invention provides sterile, pyrogen free 1,3-di-n-butyl-7-(2-oxopropyl)xanthine. The injectable compositions of this invention may consist essentially of said sterile, pyrogen free 1,3-di-n-butyl-7-(2-oxopropyl)xanthine, for example sealed into a vial or ampoule or the like. Other suitable injectable compositions of this invention may comprise said sterile material in admixture with suspending agents, preserving agents or the like. Such compositions may be made up for injection on admixture with sterile water or saline or the like. In general the volume to be injected will be from 0.5 to 2 mls, for example 1 ml.

Suitably the injectable composition of this invention will contain slightly less than the maximum orally administrable composition, for example from 1 to 25 mg of 1,3-di-n-butyl-7-(2-oxopropyl)xanthine. More suitably the injectable composition will contain 2 to 20 mg and preferably 2.5 to 15 mg of 1,3-di-n-butyl-7-(2-oxopropyl)xanthine; for example about 5, 7.5, 10 or 12.5 mgs of said agent.

Particularly favoured compositions of this invention are those adapted for oral administration since they are more convenient for general use. Such dosage forms include tablets and capsules and the like. The dosage units may contain such conventional agents as fillers (diluents), lubricants, binders, disintegrants, colourants, flavourings, surface active agents, preservatives, buffering agents and the like.

Suitable fillers for use include cellulose, manitol, lactose and other similar agents. Suitable disintegrants include starch, polyvinylpolypyrrolidone and starch derivatives such as sodium starch glycollate and the like. Suitable lubricants include stearic acid, magnesium stearate, magnesium lauryl sulphate and the like.

Since 1,3-di-n-butyl-7-(2-oxopropyl)xanthine is a medicament of high potency the solid orally administrable unit dosage form according to this invention may be small, for example under 80 mgs in weight, but for patient convenience it is usual to formulate the composition in such a manner that it weighs about 80–600 mgs, in total, for example about 100–400 mgs. This means that frequently relatively large proportions of a filler is employed. Thus formation of unit dosage forms will be simple since the skilled worker may select fillers or other agents of known physical properties to prepare the composition in conventional manner as the actual effect of the small quantity of 1,3-di-n-butyl-7-(2-oxopropyl)xanthine is slight.

The oral compositions may be prepared by conventional methods of blending, filling, tabletting or the like. Repeated blending operations may be used to distribute the active agent throughout those compositions employing large quantities of fillers. Such operations are of course conventional in the art.

The following Examples illustrate the invention:

EXAMPLE 1

1,3-Di-n-butyl-7-(2-oxopropyl)xanthine, magnesium stearate and microcrystalline cellulose were blended together and passed through a 40 mesh sieve (UK). The mixture was tabletted on a conventional rotary machine to produce a batch of 5000 tablets of the following composition.

| | |
|---|---|
| 1,3-Di-n-butyl-7-(2-oxopropyl)xanthine: | 10 mg |
| magnesium stearate: | 0.2 mg |
| microcrystalline cellulose: | 189.8 mg |

EXAMPLE 2

1,3-Di-n-butyl-7-(2-oxopropyl)xanthine, sodium lauryl sulphate, lactose and sodium starch glycollate were blended together and passed through a 40 mesh sieve (UK). The mixture was tabletted on a conventional rotary machine to produce a batch of 5000 tablets of the following composition:

| | | |
|---|---|---|
| 1,3-Di-n-butyl-7-(2-oxopropyl)xanthine: | 5 | mg |
| magnesium lauryl sulphate: | 0.1 | mg |
| lactose: | 103 | mg |
| sodium starch glycollate: | 1.9 | mg |

EXAMPLE 3

(a) 5.0 g of 1,3-di-n-butyl-7-(2-oxopropyl)xanthine were mixed with 51.04 g microcrystalline cellulose, passed through a 0.8 mm sieve with 91.35 g lactose and 2.61 g hydrogenated castor oil and mixed in a cubic mixer. The mixture was pressed into tablets of 150 mg with a single punch of diameter 7 mm, each tablet containing 5 mg of 1,3-di-n-butyl-7-(2-oxopropyl)xanthine.

(b) The mixture prepared as above was filled into capsules size 3, so that each capsule contained 150 mg of the mixture.

EXAMPLE 4

(a) 10.0 g of 1,3-di-n-butyl-7-(2-oxopropyl)xanthine were mixed with 189.8 g microcrystalline cellulose, passed through a 0.8 mm sieve with 0.2 g magnesium stearate and mixed in a cubic mixer. The mixture was pressed into tablets of 200 mg with a single punch of diameter 8 mm, each tablet containing 10 mg of 1,3-di-n-butyl-7-(2-oxopropyl)xanthine.

(b) The mixture prepared as above was filled into capsules size 0, so that each capsule contained 200 mg of the mixture.

Illustration of Pharmacological Effectiveness of Xanthine Derivatives

In the following illustrations 1,3-di-n-butyl-7-(2-oxopropyl)xanthine will be referred to as "Compound A", pentoxyphylline will be referred to as "Compound B" and 1,3-di-n-butyl-7-(2-oxobutyl)xanthine will be referred to as "Compound C".

Investigation of the effects of Compounds A,B and C upon oxygen tension and contractility of ischaemic skeletal muscle of cats Methodology:
Anaesthesia and administration of compounds:

Cats of either sex were anaesthetized with urethane/chloralose (120/60 mg/kg i.p.). In the course of the experiments, pentobarbital was injected intravenously (V. antebrachii ceph.) via a plastic tube. The intraduodenal (i.d.) application of compound was conducted by means of a plastic catheter, which was inserted into the duodenum.

(a) $pO_2$-measurements:

$pO_2$ was measured polarographically using Pt-needle electrodes (modified according to Bäumgartl and Lübbers, 1973). The reference electrode, an Ag/AgCl system was sputtered on the glass mantle of the cathode, or it was a separate electrode. The cathode was coated with a polystyrol and a collodium membrane. A constant voltage supply provided a polarizing voltage between 600 and 800 mV. The reducing current was measured by a nano-ampere amplifying meter. The cathode was inserted in the tissue by means of a motor-driven micromanipulator.

| | Characteristics of $pO_2$-electrodes | |
|---|---|---|
| characteristics | $pO_2$ needle electrode for measurement in tissues | $pO_2$ catheter electrodes for measurement in blood vessels |
| overall length | 90 mm | 15 mm |
| tip length | 5–8 mm | — |
| tip diameter | 2–4 $\mu$m | 0.7–1.2 mm |
| diameter of the measurement surface | 0.5 $\mu$m | 15 $\mu$m |
| membrane | collodium, polystyrol | 12 $\mu$m teflon, or collodium, polystyrol |
| sensitivity | $2 \times 10^{-12}$ A/Torr | $1 \times 10^{-11}$ A/Torr |
| drift | 2–5% | 1–3% |
| response time ($T_{90}$) | 0.8–1.2 sec | 2–3 sec |
| diffusion error | 1–5% | 3–6% |

Experimental procedure:

A $pO_2$-electrode was inserted in the muscle tissue (m. gastrocnemius) of both hindlegs of an anaesthetized cat. After recording the $pO_2$ of the normal perfused muscle, the blood flow to one measuring site was restricted by ligating the femoral artery. The $pO_2$ dropped steeply and the tissue became ischaemic. After a few minutes, the $pO_2$ increased and then decreased again. The values were constant after 30 to 60 min. After having reached a constant level of $pO_2$, the vehicle was given, followed by the test substance.

The recordings (Compound A i.v. vs. Compound B i.v.; Compound A i.d. vs. Compound B i.d., Compound C i.d.) were evaluated, taking one value every 10 sec—at least 36 readings being taken. The mean value and the standard deviation were calculated, in order to check the significance of the effect.

(b) Skeletal muscle contractility:

Cats of either sex were anaesthetized as for $pO_2$ measurement. After dissection of the skin of the calf muscles, the sciatic nerve was cut about 3 cm proximal to the knee. The tendon of the calf muscles was cut and connected with an isometric force transducer (SWEMA, SG 3). In order to maintain constant differences and a resting tension of 100 p, the hind limb was fixed at the tibia by means of a clamp. Direct stimulation of the muscles consisted of square wave pulses of 4 msec duration at a frequency of 2 Hz and at a voltage of 50 V. In order to keep the muscles wet and at a normal temperature, the muscles were continuously superfused by means of a NaCl-solution (0.9%, 38° C.). Femoral blood flow was restricted by a graded occlusion of the artery leading to a reduction of contractility by ca. 30%. After having reached a constant level of the contraction force, the vehicle (NaCl and Methocel, respectively) was injected, followed by the test substance.

Results:

Table 1 demonstrates that Compound A leads to a distinct increase of the contractility and pO$_2$ of ischaemic skeletal muscle. Surprisingly, Compound A shows high activity in the μg-range (50–125 μg/kg). In contrast, the dose range of activity of Compounds B and C is 5–32 mg/kg, leading to changes which are less pronounced in comparison with Compound A (see tables 1–3) at 125 μg/kg.

Table 1

| ISCHAEMIC MUSCLE - CAT | | | | |
|---|---|---|---|---|
| | contractility (% initial value) | | pO$_2$ (mmHg) (increase) | |
| | i.v. | i.d. | i.v. | i.d. |
| Compound A (dose/kg) | 36 (50 μg) | 32 (125 μg) | 10 (125 μg) | 4 (50 μg) |
| Compound B (dose/kg) | 9 (5 mg) | 23 (32 mg) | 2 (5 mg) | 3 (12.5 mg) |
| Compound C (dose/kg) | NT | 22 (12.5 mg) | NT | 6 (32 mg) |

NT = not tested because of low water solubility

Table 2

| COMPARISON COMPOUND B-COMPOUND A pO$_2$ in skeletal muscle | Cat 1.8–2.6 kg n = 6 ♂, ♀ | |
|---|---|---|
| | pO$_2$ prior to ligation (Torr ± SEM)* | pO$_2$ after ligation (Torr ± SEM)* |
| hind limb art. ligation | 20.1 ± 0.04 | 15.6 ± 0.19 |
| control | 11.0 ± 0.66 | — |
| hind limb art. ligation | 26.7 ± 0.08 | 20.6 ± 0.52 |
| control | 12.0 ± 0.02 | — |
| hind limb art. ligation | 37.4 ± 0.1 | 24.7 ± 0.64 |
| control | — | — |
| hind limb art. ligation | 27.9 ± 0.99 | 16.4 ± 1.14 |
| control | 20.1 ± 0.12 | — |
| hind limb art. ligation | 30.5 ± 0 | 12.5 ± 0.12 |
| control | 2.0 ± 0 | — |
| hind limb art. ligation | 8.2 ± 0.23 | 4.9 ± 0.23 |
| control | 13.71 ± 0.11 | — |

| | effect of Compound B 5 mg/kg i.v. Δ pO$_2$ (Torr) | effect of Compound A 125 μg/kg i.v. Δ pO$_2$ (Torr) | effect of Compound B in relation to Compound A (%) |
|---|---|---|---|
| hind limb art. lig. | 1.6 (p ≦ 0.01) | 6.2 (p ≦ 0.01) | 26.6 |
| control | 0.3 (n.s.) | 13.2 (p ≦ 0.01) | 0 |
| hind limb art. lig. | −0.16 (n.s.) | 7.3 (p ≦ 0.01) | 0 |
| control | 1.02 (p ≦ 0.01) | 3.8 (p ≦ 0.01) | 27 |
| hind limb art. lig. | −1.5 (n.s.) | 5.2 (p ≦ 0.01) | 0 |
| control | — | — | — |
| hind limb art. lig. | 4.9 (p ≦ 0.01) | 27.1 (p ≦ 0.01) | 17.9 |
| control | −2.4 (p ≦ 0.01) | 3.5 (p ≦ 0.01) | 0 |
| hind limb art. lig | 7.3 (p ≦ 0.01) | 11.2 (p ≦ 0.01) | 65.6 |
| control | 14.3 (p ≦ 0.01) | 19.3 (p ≦ 0.01) | 74.3 |
| hind limb art. lig. | 1.3 (p ≦ 0.01) | 5.6 (p ≦ 0.01) | 22.9 |

Table 2-continued

| COMPARISON COMPOUND B-COMPOUND A pO$_2$ in skeletal muscle | Cat 1.8–2.6 kg n = 6 ♂, ♀ | |
|---|---|---|
| control | −0.9 (p ≦ 0.01) | 3.4 (p ≦ 0.01) | 0 |

Mean effect of Compound B at 5 mg/kg compared to Compound A at 125 μg/kg = 21.3%
*n = between 36 and 120

Table 3

| SUBSTANCE: Compound A Formulation: aqueous solution | | Species: Weight: n: Suppliers: | Cat 1.8–2.0 kg 4 ♂, ♀ Stock/Phillips | |
|---|---|---|---|---|
| | NaCl-sal. | t (min) | dosage 50 μ/kg i.v. | t (min) |
| Δ muscle X̄ contract. ± S | ± 0 | | + 36.0* ± 21.0 | > 60 |
| Δ initial phase X̄ BP ± decrease S | ± 0 | | − 14.0* ± 8.0 | 2 |
| Δ second phase X̄ BP ± increase S | ± 0 | | + 17.0* ± 9.0 | 33 |

| | dosage 125 μg/kg i.v. | t (min) | dosage 313 μg/kg i.v. | t (min) |
|---|---|---|---|---|
| Δmuscle X̄ contract. ± S | + 19.0* ± 12.0 | > 60 | + 25.0 n = 1 | > 60 |
| Δ initial phase X̄ BP ± decrease S | − 23.1* ± 3.3 | 3 | − 25.0 n = 1 | 2 |
| Δ second phase X̄ BP ± increase S | + 10.8 ± 8.3 | 32 | + 15.0 n = 1 | 6 |

*p < 0.05
(percentage of initial values)
(t = time interval to reach initial values)
The average decrease of muscle contractility induced by the arterial occlusion was 26%.
The LD$_{50}$ in mice of 1,3-di-n-butyl-7-(2-oxopropyl)xanthine has been found to be greater than 1 g/kg per oral.

What we claim is:

1. A method of treating peripheral vascular disease in humans which comprises administering to a human in need thereof a therapeutically effective amount of 1,3-di-n-butyl-7-(2-oxopropyl)-xanthine in combination with a pharmaceutically acceptable carrier.

2. A method claim 1 wherein the peripheral vascular disease is intermittent claudication.

3. A method according to claim 1 wherein 2.5 to 90 mgs is administered per day.

4. A method according to claim 1 wherein the administration takes place twice or three times a day.

5. A method according to claim 1 wherein the administration is oral.

6. A method according to claim 1 wherein the administration is by injection.

7. A method according to claim 1 wherein the administration is by injection.

8. A method of improving blood flow in skeletal muscles in humans which comprises administering to a human in need thereof a therapeutically effective amount of 1,3-di-n-butyl-7-(2-oxopropyl)-xanthine in combination with a pharmaceutically acceptable carrier.

* * * * *

UNITED STATES PATENT AND TRADEMARK OFFICE
CERTIFICATE OF CORRECTION

PATENT NO. : 4,225,607
DATED : September 30, 1980
INVENTOR(S) : Joachim Ewald Goring et al It is certified that error appears in the above-identified patent and that said Letters Patent are hereby corrected as shown below:

Col. 3, line 53, change "(2-oxobutyl)" to --(3-oxobutyl)--.

Signed and Sealed this

Tenth Day of January, 1989

Attest:

DONALD J. QUIGG

*Attesting Officer*   *Commissioner of Patents and Trademarks*

Disclaimer 4,225,607.—*Joachim E. Goring; Peter P. Ochlich*, both of Gronau, Fed. Rep. of Germany. PHARMACEUTICAL COMPOSITION CONTAINING A XANTHINE DERIVATIVE. Patent dated Sept. 30, 1980. Disclaimer filed Sept. 2, 1988, by the assignee, Beecham-Wulfing GmbH & Co. KG.

Hereby enters this disclaimer to claim 8 of said patent.

[ *Official Gazette June* 6, 1989 ]